United States Patent [19]

Croomes et al.

[11] 4,200,608
[45] Apr. 29, 1980

[54] DETECTOR FOR FUMES OF HYDRAZINE AND ITS DERIVATIVES

[75] Inventors: Edgar F. Croomes, Athens; James A. Murfree, Huntsville, both of Ala.

[73] Assignee: The United States of America as represented by the Secretary of the Army, Washington, D.C.

[21] Appl. No.: 915,706

[22] Filed: Jun. 15, 1978

[51] Int. Cl.$^2$ .................... G01N 27/02; G01N 27/16; G01N 31/10
[52] U.S. Cl. .................................. 422/97; 23/232 E; 73/26; 338/34; 422/98
[58] Field of Search ................. 23/232 E; 422/94–97; 73/25, 26, 27 R; 338/34; 324/71 SN

[56] References Cited

U.S. PATENT DOCUMENTS

| | | | |
|---|---|---|---|
| 3,200,011 | 8/1965 | Baker | 422/97 |
| 3,354,052 | 11/1967 | Williams | 73/25 |
| 3,479,257 | 11/1969 | Shaver | 338/34 |
| 3,549,329 | 12/1970 | Silverman | 422/96 |
| 3,564,474 | 2/1971 | Firth et al. | 422/95 |
| 3,960,495 | 6/1976 | Tautram | 23/232 E |
| 3,961,248 | 6/1976 | Kawamura et al. | 324/71 SN |
| 4,002,429 | 1/1977 | Bartovsky et al. | 422/96 |
| 4,029,472 | 6/1977 | Micheli et al. | 60/276 |
| 4,045,177 | 8/1977 | McNally | 338/34 |
| 4,063,898 | 12/1977 | Fisher | 23/232 E X |
| 4,072,467 | 2/1978 | Jones | 338/34 |

FOREIGN PATENT DOCUMENTS 1,006,630   8/1957   Fed. Rep. of Germany ......... 73/25

Primary Examiner—Michael S. Marcus
Attorney, Agent, or Firm—Nathan Edelberg; Robert P. Gibson; Jack W. Voigt

[57] ABSTRACT

Disclosed is a detector for fumes of hydrazine and its derivatives, methylhydrazine (MMH) and 1,1-dimethylhydrazine (UDMH). The detector encompasses a means for generating heat when fumes of hydrazine or its derivatives are catalytically decomposed after coming in contact with the active ingredient of the detector. The means for generating heat includes the active ingredient, iridium, which is deposited within and upon a ceramic pellet. The pellet is fitted with a thermal responsive means responsive to the generated heat. An output signal proportional to the generated heat can be interpreted by a balanced electronic bridge. The electronic bridge is balanced by preparing an unimpregnated pellet in the same way as the impregnated pellet and putting it in the circuit as a reference. The reference, being the same size and shape and prepared in the same manner, compensates for changes in temperature and other changes in the circuit, thus allowing one to zero the instrument. When the impregnated pellet comes into contact with fumes of hydrazine, MMH or UDMH, an imbalance is caused. The potential difference may be monitored by a meter, recorder, bell signal, etc. Neither the heat nor the catalytic action depletes the iridium or its action upon fumes of hydrazine and its derivative compounds.

2 Claims, 2 Drawing Figures

DETECTOR FOR FUMES OF HYDRAZINE AND ITS DERIVATIVES

DEDICATORY CLAUSE

The invention described herein may be manufactured, used, and licensed by or for the Government for governmental purposes without the payment to us of any royalties thereon.

BACKGROUND OF THE INVENTION

Hydrazine ($N_2H_4$) and its derivative compounds have been used extensively as fuels in rockets and missile systems. Since most of these systems are designed to be stored for long periods of time, a constant surveillance of the storage environment is essential. Also required is constant monitoring of the storage area for toxic fumes of these fuels.

Considerable efforts have been expanded in developing detectors for the toxic fumes of hydrazine and its derivative compounds. These detectors have yielded satisfactory results in detecting the presence of these fumes through chemical reaction between the fumes and a reactant which yielded a color change or other changes detectable by a sensor. The prior art detectors have experienced depletion in the reactor portion or have been good for a one use performance. The prior art detectors will be discussed further below by citing examples and relating some of the inadequacies experienced.

One detector system employed a chemical reaction in conjunction with an electronic readout system. The fault with this system was that the chemical reaction depleted the sensor, thus rendering the detector useless until replenished or replaced, although the electronic portion would still calibrate properly.

The most successful detector to date is the glass tube filled with a reactant upon a substrate. The reaction between the reactant and hydrazine vapor produces a distinctive color change. Indicator papers are made in the same way and are also used as detectors. The tubes and papers are used only once.

A detector system for fumes of hydrazine and its derivatives which does not employ a chemical reaction that depletes the active ingredient of the detector system would be more desirable.

Also advantageous would be a detector system for fumes of hydrazine and its derivatives which can be made very small, which can employ an electronic readout component, and which can be placed long distances from its electronic readout component to thereby provide monitoring performance of a storage facility without endangering the operator.

Therefore an object of this invention is to provide a detector for fumes of hydrazine and its derivatives which employs a sensor which is used repeatedly with minimal or no degradation of the active ingredient.

Another object of this invention is to provide a detector for fumes of hydrazine and its derivatives which can be easily calibrated for use with an electronic readout system.

A further object of this invention is to provide a detector for fumes of hydrazine and its derivatives which can be made very small for use with miniaturized electronic readout circuits.

Still a further object of this invention is to provide a detector for fumes of hydrazine and its derivatives which can be located long distances from its electronic readout circuitry whereby monitoring performance of a storage facility can be achieved without endangering the operator.

SUMMARY OF THE INVENTION

The catalyst, iridium, decomposes fumes of hydrazine and its derivative compounds, methylhydrazine and 1,1-dimethylhydrazine, with heat being liberated in the area of decomposition. This is the reaction utilized for the detector for hydrazine and its derivative compounds.

The detector of this invention employs a ceramic pellet within and upon which iridium is deposited. The detector employs another ceramic pellet as a reference which is not impregnated along with the impregnated pellet which serves to balance an electronic circuit. The reference, being the same size and shape and prepared in the same manner, compensates for changes in temperature and other changes in the circuit, thus allowing one to zero the detector. When the impregnated pellet is contacted with fumes of hydrazine, MMH, or UDMH, an imbalance is caused which is measurable as a potential difference. This potential difference may be monitored by a meter, recorder, or used to actuate a bell signal etc.

Since neither the heat nor the catalytic action is depleting to the iridium, the iridium has a substantially unlimited reactive period for catalyzing the decomposition of hydrazine, MMH, or UDMH.

BRIEF DESCRIPTION OF THE DRAWING

The FIGURES of the drawing illustrate a detector system circuitry and the detecting pellet of the detector system for monitoring fumes from hydrazine, MMH, or UDMH.

DESCRIPTION OF THE PREFERRED EMBODIMENT

Hydrazine, MMH, and UDMH are catalytically decomposed by iridium catalyst of an impregnated pellet. The impregnated pellet is fitted with a thermal detector which is sensitive to the heat generated in the area of decomposition. The impregnated pellet with the thermal detector and an unimpregnated pellet are part of a balanced electronic bridge. The balanced electronic bridge results by preparing an unimpregnated pellet in the same way as the impregnated pellet and placing it in the circuit with the unimpregnated as a reference. The reference, being the same size and shape and prepared in the same manner, compensates for changes in temperature and other changes in the circuit, thus allowing one to zero the detector of this invention. When fumes of hydrazine, MMH, or UDMH come into contact with the impregnated pellet an imbalance results. The imbalance or potential difference may be recorded on a meter, recorder, or may be used to actuate a bell signal to indicate the presence of hydrazine fumes in the area.

A typical detecting pellet can be constructed of any suitable size. A representative sized pellet measures one-fourth inch in diameter by one-fourth inch in height and may be of the aluminum oxide type, such as Harshaw 1404-T. For the unimpregnated pellet, the pellet is used as-received. For the impregnated pellet, it has been found satisfactory to use an iridium-coated aluminum oxide pellet distributed under the name "Shell 405". The iridium-coated aluminum oxide pellet can be prepared by repeated soaking in chloroiridic acid solution, followed by drying and reduction with hydrogen. By repetition of these steps, a coating of iridium in the range of 28 to 36 percent by weight iridium in or on the pellet may be obtained.

Figure 1:
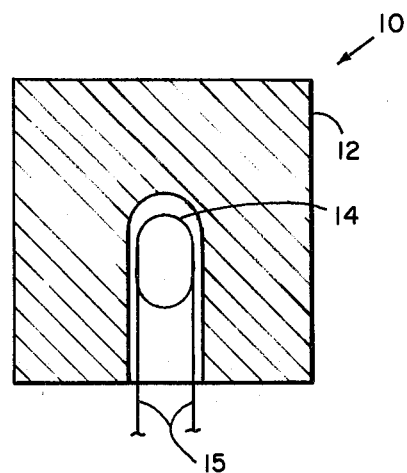

In further reference to the Figures of the drawing, FIG. 1 shows the detector 10 of this invention. The detector is comprised of an iridium-impregnated pellet 12 with a thermistor 14 (or other heat detecting device such as a thermocouple) embedded in the impregnated pellet. Conductive leads are shown as 15 for connecting to an electrical circuit.

Figure 2:
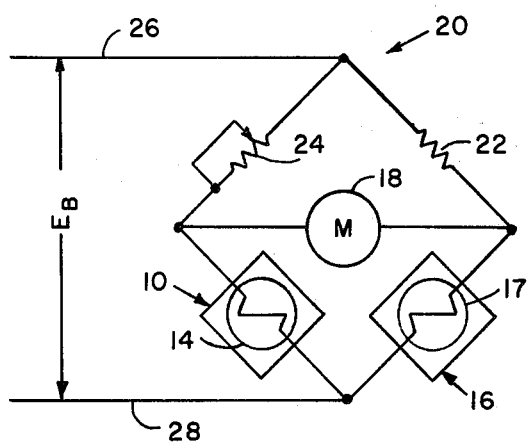

FIG. 2 shows a balanced bridge circuit 20 employing the detector 10, as described in FIG. 1, along with an unimpregnated pellet 16 having a thermistor or thermocouple 17 embedded therein as a reference. A differential measuring means is designated M with an assigned numeral 18. The other elements of the balanced bridge include a resistor 22 and a variable resistor 24. A voltage source $E_B$ is applied to circuitry to achieve a constant voltage between lins 26 and 28.

Prior to use, the Wheatstone Bridge Circuitry 20 is balanced to read zero by the variable resistor 24. After exposure to hydrazine fumes a voltage differential is developed between 14 and 17 which is measurable by the differential measuring means 18 because the unimpregnated pellet will not be affected by the chemicals of interest and remains at ambient temperature, whereas the impregnated pellet, when exposed to the hydrazine fumes (or vapors), becomes warm as a result of the catalyzed exothermic decomposition of the fumes of hydrazine on the iridium-impregnated pellet. This heat release results in an off-balance signal from the thermistor (or other heat detecting device) embedded in the impregnated pellet. Because of the lack of change in the temperature of the unimpregnated pellet, when in contact with hydrazine vapors, no off-balance signal is given off by the thermistor (or other heat detecting device) embedded in the unimpregnated pellet. When the electronic bridge goes off balance, a voltage results which, either amplified or unamplified, may be monitored or recorded or used to drive an alarm device, either audible and/or visual.

In operation, the detector would be arranged such that the impregnated and unimpregnated pellets, together in a suitable holder, would act as a detector head when placed in the environment which is to be monitored for hydrazine vapor presence. The suitable holder could be of any particular design which would offer protection to the detector element and circuitry plus ensures that fumes can contact the impregnated pellet through a perforated holder, screened holder, or the like. The electronic and alarm devices may be located separately and remotely from the head and connected through suitable electrical connections. The impregnated and unimpregnated pellets would be electrically balanced on the electronic bridge circuit in an atmosphere free of hydrazine. After balancing, the presence of hydrazine vapor in the vicinity of the detector head would be detected by the fact that the vapor would decompose exothermally on the iridium-impregnated pellet, thus evolving heat which would result in an off-balance signal. Since there is no reaction on the unimpregnated pellet, the signal remains constant. This combination results in the bridge going off balance, with a resultant voltage being produced which can be amplified, if necessary, to drive a recording device of alarm system. Resetting the detector would consist only of balancing the bridge when the detector head is in a hydrazine-free atmosphere. Thus, the output from an in-service detector is proportional to the hydrazine fumes which are catalytically decomposed as interpreted from the heat rise in the impregnated pellet.

We claim:

1. A detector for fumes of hydrazine and its derivatives, methylhydrazine and 1,1-dimethylhydrazine comprising in combination:
   (i) a pellet of aluminum oxide impregnated with the catalyst material iridium, said iridium comprising from about 28 to about 36 percent by weight of said pellet for catalytically decomposing said fumes when said fumes make contact with said iridium of said impregnated pellet to cause heat to be generated in said pellet;
   (ii) thermally responsive thermistor means or thermocouple means embedded in said pellet responsive to said generated heat for providing an output signal proportional to said generated heat.

2. The detector of claim 1 in combination with a bridge circuit wherein said bridge circuit includes an unimpregnated pellet of like construction to that of said impregnated pellet except unimpregnated pellet does not contain iridium, said unimpregnated pellet functioning as a reference for balancing said bridge circuit in an atmosphere free of said fume prior to said detector being placed in service, said detector in said balanced bridge circuit after being exposed to said fumes causing an off-balance output signal which can be monitored for equating said signal to the amount of said fumes.

* * * * *